United States Patent
Van Dongen et al.

(10) Patent No.: US 10,668,168 B2
(45) Date of Patent: Jun. 2, 2020

(54) METHOD FOR REMOVING WEAKLY BOUND FUNCTIONAL MOIETIES FROM CELL TARGETING CONJUGATES

(71) Applicant: LinXis B.V., Breda (NL)

(72) Inventors: Augustinus A. M. S. Van Dongen, Utrecht (NL); Niels Jurriaan Sijbrandi, Utrecht (NL); Dennis Christian Johannes Waalboer, Umuiden (NL); Hendrik Jan Houthoff, Amsterdam (NL)

(73) Assignee: LinXis B.V., Breda (NL)

( * ) Notice: Subject to any disclaimer, the term of this patent is extended or adjusted under 35 U.S.C. 154(b) by 0 days.

(21) Appl. No.: 15/556,764

(22) PCT Filed: Mar. 9, 2016

(86) PCT No.: PCT/NL2016/050163
§ 371 (c)(1),
(2) Date: Sep. 8, 2017

(87) PCT Pub. No.: WO2016/144171
PCT Pub. Date: Sep. 15, 2016

(65) Prior Publication Data
US 2018/0055947 A1  Mar. 1, 2018

(30) Foreign Application Priority Data
Mar. 9, 2015 (NL) .................................... 2014423

(51) Int. Cl.
*A61K 47/68* (2017.01)
*A61K 47/02* (2006.01)

(52) U.S. Cl.
CPC .......... *A61K 47/6855* (2017.08); *A61K 47/02* (2013.01); *A61K 47/68* (2017.08)

(58) Field of Classification Search
CPC ..... A61K 47/6855; A61K 47/68; A61K 47/02

USPC .......................................................... 548/101
See application file for complete search history.

(56) References Cited

U.S. PATENT DOCUMENTS

2014/0377174 A1   12/2014   Houthoff et al.

FOREIGN PATENT DOCUMENTS

| EP | 1745802 A1 | 1/2007 |
|---|---|---|
| WO | 2013103301 A2 | 7/2013 |
| WO | 2016144171 A1 | 9/2016 |

OTHER PUBLICATIONS

Waalboer et al., Platinum(II) as Bifunctional Linker in Antibody-Drug Conjugate Formation: Coupling of a 4-Nitrobenzo-2-oxa-1,3-diazole Fluorophore to Trastuzumab as a Model, Chemmedchem, May 25, 2015, pp. 797-803, vol. 10, No. 5.
PCT International Search Report, PCT/NL2016/050163, dated Jun. 24, 2016.
PCT International Written Opinion, PCT/NL2016/050163, dated Jun. 24, 2016.
Temming et al., Delivery of the p38 MAPkinase Inhibitor SB202190 to Angiogenic Endothelial Cells: Development of Novel RGD-Equipped and PEGylated Drug-Albumin Conjugates Using Platinum(II)-Based Drug Linker Technology, Bioconjugate Chemistry, Sep. 1, 2006, pp. 1246-1255, vol. 17, No. 5.
European Communication pursuant to Article 94(3) EPC for European Application No. 16718509, dated Aug. 14, 2019, 4 pages.

*Primary Examiner* — Kristin A Vajda
(74) *Attorney, Agent, or Firm* — TraskBritt (57) ABSTRACT

This disclosure describes a method for preparing stable cell targeting conjugates. A further aspect of this disclosure relates to the stable cell targeting conjugates obtainable by the method and to pharmaceutical compositions comprising these stable cell targeting conjugates. A last aspect of this disclosure relates to the use of these conjugates and pharmaceutical compositions as a medicament.

13 Claims, 2 Drawing Sheets

METHOD FOR REMOVING WEAKLY BOUND FUNCTIONAL MOIETIES FROM CELL TARGETING CONJUGATES

CROSS-REFERENCE TO RELATED APPLICATIONS

This application is a national phase entry under 35 U.S.C. § 371 of International Patent Application PCT/NL2016/050163, filed Mar. 9, 2016, designating the United States of America and published in English as International Patent Publication WO 2016/144171 A1 on Sep. 15, 2016, which claims the benefit under Article 8 of the Patent Cooperation Treaty to The Netherlands Patent Application Serial No. 2014423, filed Mar. 9, 2015.

TECHNICAL FIELD

This application relates to a method for preparing stable cell targeting conjugates. This disclosure further relates to the stable cell targeting conjugates obtainable by the method and to pharmaceutical compositions comprising these stable cell targeting conjugates.

BACKGROUND

Site-specific or targeted delivery of drugs is considered a valuable tool to improve the therapeutic efficacy and to reduce the toxicity of drugs. For example, antibody-drug-conjugates are known in the art and may, for example, consist of a recombinant antibody covalently bound to a small therapeutic compound (typically 300 to 1,000 Da) via a synthetic linker (S. C. Alley et al., *Curr. Opin. Chem. Biol.* 2010, 14:529-537).

Whereas non-targeted drug compounds or diagnostic compounds typically reach their intended target cells via whole-body distribution and passive diffusion or receptor mediated uptake over the cell membrane, targeted drugs or targeted diagnostic compounds home-in and concentrate mainly at the targeted tissues. Consequently, targeted drugs (herein meant as drugs targeted by a targeting moiety) or diagnostic compounds require smaller dosages while still allowing the drug to reach therapeutically or diagnostically effective levels inside or at the level of the target lesion or cells and thus improving the therapeutic or diagnostic window.

In this regard it is important to note that in general it is favorable if the amounts of targeted therapeutic compounds that reach the target cells can be adjusted according to their efficacy, in other words that the accumulation of therapeutic compounds at the target cell needs to be higher in case they are less potent (e.g., less cytotoxic). For diagnostic compounds, a high accumulation at the target cell is generally considered advantageous, unless this reduces the signal as, e.g., in case of quenching.

The use of targeted diagnostic compounds is of great value for whole body imaging and can be used for patient selection and response prediction for targeted therapeutics (personalized medicine) and for validation of therapeutic responses to targeted therapeutic compounds.

The targeting of therapeutic compounds or diagnostic compounds to specific cells is thus a conceptually attractive method to enhance specificity, to decrease systemic toxicity compared to conventional delivery and to allow for the therapeutic or in-vivo diagnostic use of compounds that are in principle less suitable or unsuitable as systemic drugs. Drug targeting is achieved when an alteration in the drug's bio-distribution favors drug accumulation at the desired site, which site is usually remote from the administration site. Cell-selective delivery of therapeutic agents (drugs) can, in principle, be obtained by coupling drug molecules to targeting moieties which targeting moieties are a member of a specific binding pair, i.e., a member from a pair of molecules wherein one of the pair of molecules has an area on its surface or a cavity which specifically binds to, and is, therefore, defined as complementary with, a particular spatial and polar organization of the other molecule, so that the pair have the property of binding specifically to each other. Examples of types of specific binding pairs are antigen-antibody, biotin-avidin, hormone-hormone receptor, receptor-ligand, enzyme-substrate, IgG-protein A. Particularly suitable targeting moieties from such binding pairs are macromolecular carriers, such as, for example, monoclonal antibodies, antibody fragments or engineered variants thereof or low molecular weight carriers, such as, for example, peptides.

However, the linkage between the therapeutic compound and the targeting moieties often poses significant problems. For instance, the linking of lipophilic non-targeted therapeutic compounds to hydrophilic targeting moieties may be difficult, Furthermore, chemically reactive groups for conventional conjugation chemistry may be absent, or chemically reactive groups may be (abundantly) present, but (covalent) linkage may (irreversibly) inhibit the bioactivity of the coupled therapeutic compound.

In International Patent Application WO 2013/103301 methods are described for linking therapeutic compounds to targeting moieties by using (transition) metal ion complexes as a linker between the therapeutic compounds and the targeting moieties. This way, cell targeting conjugates are prepared, which work well in-vivo.

However, analyses have shown that a fraction of the functional moiety and platinum linker may detach from the binding site on the targeting moiety. In a clinical setting this would result in the presence of free functional moieties, such as (super) toxic drugs and free platinum in the body. Hence, a need exists for cell targeting conjugates that are more stable, i.e., wherein the functional moieties do not detach from the binding site on the targeting moieties outside the intended place of action.

BRIEF SUMMARY

This disclosure relates to a method for preparing stable cell targeting conjugates, comprising:
  (a) providing a composition of cell targeting conjugates, which conjugates comprise a targeting moiety and one or more functional moieties bound thereto via a linker, which linker comprises a transition metal complex;
  (b) treating the composition of cell targeting conjugates with an agent that removes weakly bound functional moieties from the cell targeting conjugates, such that a composition comprising stable cell targeting conjugates is obtained.

With the method according to the disclosure, it has now become possible to remove weakly bound functional moieties from the targeting moiety, such as antibodies or fragments thereof. This way, stable cell targeting moieties are obtained, which are well suited to be used clinically.

This disclosure further relates to stable cell targeting conjugates obtainable by the above-mentioned method. These cell targeting conjugates are more stable than nontreated conjugates. This allows, amongst others, a better storage stability and (more importantly) a broader therapeutic window.

A further aspect of this disclosure relates to a pharmaceutical composition comprising the above-mentioned stable cell targeting conjugates.

A last aspect of this disclosure relates to the use of these stable cell targeting conjugates as a medicament or as a label.

Definitions

The term "linker" as used herein generally has its conventional meaning and thus refers to a chemical moiety that forms a bridge-like structure between a targeting moiety and a functional moiety, such that the latter two are bound to each other.

The term "functional moiety" as used herein refers to a chemical group or molecule, which has a certain biological, chemical, therapeutic and/or diagnostic function ex vivo or in vivo. Typical functional moieties are therapeutic compounds (i.e. drugs) or diagnostic compounds (i.e. tracers or dyes).

The term "targeting moiety" as used herein refers to a member of a specific binding pair, i.e. a member of a pair of molecules wherein one of the pair of molecules, has an area on its surface, or a cavity which specifically binds to, and is, therefore, defined as complementary with a particular spatial and polar organization of the other molecule, so that the pair have the property of binding specifically to each other. Examples of types of specific binding pairs are antigen-antibody, biotin-avidin, hormone-hormone receptor, receptor-ligand, enzyme-substrate, IgG-protein A.

The term "removal of weakly bound functional moieties" as used herein refers to the breakage and removal of specific chemical groups from a molecule. Within the context of this disclosure, removal thus refers to the breakage or the prevention of the bond of weak (also referred to as labile) bonds between the linker and binding sites on the targeting moiety.

The term "separating" as used herein has its normal scientific meaning and refers to the separation of one species, such as a chemical compound from another species, such as a solvent. Within the context of the present application separating may be done at once or may be done in different steps, which steps may also be carried out at different locations.

The term "specific binding pair" as used herein refers to a member from a pair of molecules wherein one of the pair of molecules has an area on its surface or a cavity which specifically binds to, and is, therefore, defined as complementary with, a particular spatial and polar organization of the other molecule, so that the members of the pair have the property of binding specifically to each other. Examples of types of specific binding pairs are antigen-antibody, biotin-avidin, hormone-hormone receptor, receptor-ligand, enzyme-substrate, IgG-protein.

The term "targeted drug" as used herein refers to a drug coupled to a targeting moiety such as an antibody.

The term "immunoreactivity" as used herein has its normal scientific meaning and refers to the binding affinity of a member of a specific binding pair, such as a peptide, an antibody, an antibody fragment or engineered variant thereof.

DETAILED DESCRIPTION

A first aspect of the disclosure relates to a method for preparing stable cell targeting conjugates, comprising:
(a) providing a composition of cell targeting conjugates, which conjugates comprise a targeting moiety and one or more functional moieties bound thereto via a linker, which linker comprises a transition metal complex;
(b) treating the composition of cell targeting conjugates with an agent that removes weakly bound functional moieties from the cell targeting conjugates, such that a composition comprising stable cell targeting conjugates is obtained.

With the method of the disclosure, it has now become possible to remove weakly bound functional moieties from targeting moieties. This way, stable cell targeting conjugates are obtained that are more stable and do not show, or at least to a lesser extent, a detachment of the functional moieties from the targeting moieties.

An important advantage thereof is that the therapeutic window significantly increases. After all, due to the fact that less functional moieties detach from the targeting moiety, higher doses of these stable cell targeting conjugates may be used. A further advantage of the method of this disclosure and the stable cell targeting conjugates obtained therewith is that they have a better shelf life and can be stored for prolonged periods of times without significant amounts of functional moieties detaching from the targeting moieties.

The cell targeting conjugates which are provided in step a) have preferably been coupled under relatively mild conditions. In this regard the term "mild conditions" means that the reaction conditions are chosen such that the immunoreactivity of the targeting moieties stays substantially the same as the immunoreactivity of the unbound targeting moieties. Within this context, the wording "substantially the same immunoreactivity as the unbound targeting moieties" means that the reaction conditions or the amount of functional moieties bound to the targeting moiety has not significantly impaired the immunoreactivity, i.e., the binding affinity, of the targeting moiety. The immunoreactivity, i.e., the binding affinity, as referred to herein may be measured by a binding assay as described in T. Lindmo (*J. Immunol. Methods* 72:77-89, 1984). Furthermore, the immunoreactivity may also be determined by BIACORE® analysis.

The most preferred conditions for coupling the functional moieties with the targeting moieties via the linkers of this disclosure are if the pH is between 5 and 9, preferably between 7 and 9, the temperature is about 37° C. and wherein the reaction time is as short as possible, such as 10 to 240 minutes. This means that if, for example, a higher reaction temperature is used, a shorter reaction time should be used. The same applies to pH. If a higher or lower pH is used, the reaction time should be decreased in order to avoid loss of the immunoreactivity of the targeting moiety.

With respect to the preferred reaction conditions under which the cell targeting conjugates of step a) have preferably been prepared; reference is made to the International Patent Application WO 2013/103301, which is herewith incorporated herein by reference.

In the cell targeting conjugates provided in step a) the linkers attached to the functional moieties have formed so called "coordination bonds" with binding sites on the targeting moiety. This way, the functional moieties are bound via the linkers to a targeting moiety.

Furthermore, linkers comprising a transition metal complex have a tendency to bind to histidine residues and cysteine residues if present and available in the targeting moiety, e.g., an antibody or fragment thereof. The linkage, i.e., coordination bond, between these types of linkers and these residues on the targeting moiety is very strong and are thus stable and not easily broken.

However, besides binding to these residues, it has been reported that these types of linkers also bind to, e.g., methionine and cysteine sulfur-bridges present in the targeting moiety. Unfortunately, the strength of such bonds is relatively low. In other words, the coordination bond between these two is labile. This means that in a clinical setting, or even during storage, such a bond between the linker and the targeting moiety may be broken and that functional moieties bound via such linkers to the targeting moiety easily detach therefrom. This limits the therapeutic window of these kinds of cell targeting conjugates as well as their storage stability.

By carrying out a further step wherein these weakly bound functional moieties are removed from the targeting moiety, the above-mentioned problems can be avoided. In this further step b) an agent capable of selectively removing the weakly bound functional moieties is added to the cell targeting conjugates of step a).

The agent used has a relative binding affinity for the linker that is higher than the relative binding affinity of the linker for the unwanted binding sites on the targeting moiety, such as methionine and cysteine sulfur bridges. This way, the linker (together with the functional moiety connected therewith) is detached from the (unintended) binding site of the targeting moiety and binds to the agent. Hence, weakly bound functional moieties are removed from the cell targeting conjugates.

However, in order to avoid that the agent also detaches linkers, which are strongly bound to the targeting moiety, the relative binding affinity of the agent for the linker has to be lower than the relative binding affinity of the linker for the intended binding sites of the targeting moiety. More specifically, the relative binding affinity of the agent for the linker is preferably lower than the relative binding affinity of the linker for histidine.

Although it is preferred to carry out step b) after the cell targeting conjugates have been prepared, it is also possible to use the agent during the preparation of the cell targeting conjugates, as has been described above. In other words, step a) and b) may be combined in one single step.

In a further step c) the stable cell targeting conjugates obtained in step b) are separated from the composition. Separation of the conjugates may be carried out by means of filtration or chromatographic methods, preferably by means of size exclusion chromatography. It is particularly preferred to use so called PD10 columns for separating the stable cell targeting conjugates from the reaction mixture.

In a preferred embodiment, the linker comprises a platinum complex. The platinum complex may be a trans-platinum complex or it may be a cis-platinum complex. The cis-platinum complex is preferred and comprises preferably an inert bidentate moiety as a stabilizing bridge. In another embodiment the (platinum) metal ion complex comprises a tridentate moiety as a stabilizing bridge.

The agent for removing the weakly bound functional moieties is preferably a so called "S-donor." These compounds can be provided either in solution or on a solid support.

Agents for use in the method according to the disclosure are thiourea, sodium thiosulphate (STS), glutathione, cysteine, N-acetylcysteine, potassium thiocyanate, sodium thiocyanate, biotin, methionine, n-acetyl-methionine penicillamine, mesna or combinations thereof.

After step b) has been carried out a significant reduction of the number of weakly bound functional moieties has taken place. Hence, this ratio (also referred to as the DAR, i.e., drug antibody ratio) in the stable cell targeting conjugates is preferably between 5:1 and 1:1.

The composition wherein the above-mentioned method is carried out, is preferably an aqueous solution or dispersion.

The functional moiety is in a preferred embodiment of this disclosure a therapeutic compound, a diagnostic compound or a chelating agent.

It is particularly preferred when the functional moiety is a therapeutic compound that inhibits a signal transduction cascade in a cellular system, interferes with the cytoskeleton or intercalates in the DNA double helix. It is further preferred that the functional moiety has anti-inflammatory, anti-hypertensive, anti-fibrotic, anti-angiogenic, anti-tumor, immune-stimulating or apoptosis-inducing activity, preferably the therapeutic compound has an anti-tumor activity.

According to the disclosure, the functional moiety may be a therapeutic compound chosen from the group of kinase inhibitors, or pro-drugs thereof. In another embodiment of the disclosure, the kinase inhibitor is erlotinib, gefitinib, imatinib, pentoxifylline, PDTC, PTKI, SB202190, vatanalib, LY364947, Y27632, AG1295, SP600125.

Alternatively, the functional moiety chosen is an angiotensin receptor blocker, such as losartan.

Alternatively, the functional moiety is a recombinant protein, such as TNF-related apoptosis-inducing ligand (TRAIL). Alternatively, the functional moiety is a therapeutic radionuclide, such as the beta emitters 90Y or 177Lu, or the alpha emitter 211At.

Alternatively, the functional moiety is a (super-)toxic drug chosen from the group of taxanes, anthracyclines, vinca alkaloids, calicheamicins, maytansinoids, auristatins, tubulysins, duocarmycins, or pyrrolobenzodiazapine analogs.

Besides using therapeutic compounds as the functional moiety, diagnostic compounds can also be used. In an alternative embodiment, the functional moiety is a fluorescent dye, such as IRDye800CW, DY-800, DY-831, ALEXA FLUOR® 750, ALEXA FLUOR® 790, and indocyanine green.

Other diagnostic compounds, which may be used in this disclosure as functional moieties are radionuclides, PET-imageable agents, SPECT-imageable agents or MRI-imageable agents.

It is also possible to couple chelating agents as a functional moiety via the linker to the targeting moiety. These chelators may, prior or after coupling to the targeting moiety, be loaded with therapeutic or diagnostic radionuclides or non-radioactive metals. Possible chelating agents are EDTA, DPTA and desferioxamine. However, macrocyclic chelating agents may also be used, such as DOTA or p-SCN-Bn-DOTA, to which a transition metal PET radioisotope, a non-radioactive metal, or transition metal SPECT radioisotope, such as $^{99m}$Tc or $^{195m}$Pt is coupled.

Alternatively, more than one kind of functional moiety is used. This way, it is possible to bind different functional moieties, e.g., different useful combinations of therapeutic compounds or different combinations of useful diagnostic compounds to one targeting moiety. This way, a preferred combination of therapeutic compounds can be delivered to the tissue of interest.

In order to obtain a bond with adequate stability for in vivo applications it is preferred that the targeting moiety and/or the functional moiety comprise one or more sulfur-containing reactive sites and/or one or more nitrogen containing sites. It is particularly preferred that the functional moiety, such as a therapeutic compound, comprises one or more sulfur groups and/or one or more nitrogen groups, preferably heterocyclic or aliphatic amines or aromatic nitrogen groups. The targeting moiety, preferably comprises histidine and/or cysteine residues, which may be used as binding sites for the linker and the functional moiety attached to the linker.

The targeting moiety is preferably a peptide, an antibody, an antibody fragment or engineered variant thereof.

The targeting moiety preferably comprises a member of a specific binding pair and is thus able to bind to distinctive parts of certain cells or tissues. This way, the targeting moiety is able to bring the functional moiety, which is attached thereto via the linker, to the place of interest.

The targeting moiety may comprise antibodies, such as monoclonal antibodies, derivatives or fragments thereof or may comprise peptides.

A derivative of an antibody is defined herein as an antibody which has been altered such that at least one property—preferably an antigen-binding property—of the resulting compound is essentially the same in kind, not necessarily in amount. A derivative is provided in many ways, for instance, through conservative amino acid substitution, whereby an amino acid residue is substituted by another residue with generally similar properties (size, hydrophobicity, etc.), such that the overall functioning is likely not to be seriously affected.

A fragment of an antibody is defined as a part that has at least one same property as the antibody in kind, not necessarily in amount. The functional part is capable of binding the same antigen as the antibody, albeit not necessarily to the same extent. A fragment of an antibody preferably comprises a single domain antibody (also referred to as nanobody), a single chain antibody, a single chain variable fragment (scFv), a Fab fragment or a F(ab')2 fragment. Suitably, the targeting moiety is a monoclonal antibody, most preferably a monoclonal antibody chosen from the group of antibodies which have shown a capacity for selective tumor targeting, such as adalimumab, bevacizumab, catumaxomab, cetuximab, gemtuzumab, golimumab, infliximab, panitumumab, rituximab and trastuzumab or combinations thereof.

Alternatively, the targeting moiety is an antibody fragment or engineered variant thereof, such as a therapeutic FAB, such as ranibizumab, a diabody, a minibody, a domain antibody, an affibody, a nanobody, such as ALX-0651, or an anticalcin.

A further aspect of this disclosure relates to the stable cell targeting conjugates obtainable by the above-mentioned method. Due to the method with which these stable cell targeting conjugates have been prepared, they have properties which have not been observed before.

After all, up till now; cell targeting conjugates of the types described in International Patent Application WO 2013/103301 always comprised many functional moieties, which were relatively weakly bound to (unintended) binding sites of the targeting moiety, typically through their linker. However, in the stable cell targeting conjugates according to this disclosure, a considerable number of such weakly bound functional moieties has been removed.

The difference between the stable cell targeting conjugates of the disclosure and the conjugates known in the prior art can easily be determined by storing the cell targeting conjugates at room temperature for 48 hours in a storage buffer. Size exclusion chromatography of the compositions will show that in the composition wherein the stable cell targeting conjugates were stored, no significant amount of detached functional moiety or functional moiety-linker complex is observed. In the composition comprising the untreated and thus unstable cell targeting conjugates, a considerable amount of detached functional moiety or functional moiety-linker complex will be observed. Typically, from the stable cell targeting conjugates according to this disclosure, less than 10%, preferably less than 5% of the functional moieties initially bound thereto will be released during the above-mentioned treatment in PBS. The untreated cell targeting conjugates will show a considerably higher percentage of release than the cell targeting conjugates, which have been prepared with the method according to this disclosure. In this regard, reference is also made to the examples below.

The cell targeting conjugates according to this disclosure have a serum stability, which is at least two times larger than the serum stability of untreated conjugates. Methods for determining the serum stability of cell targeting conjugates are well known in the art.

Furthermore, as already mentioned above, with the stable cell targeting conjugates of the disclosure, a larger therapeutic window and better storage stability is obtained.

In the stable cell targeting conjugates according to this disclosure, preferably on average 1 to 5, preferably 2 to 3 functional moieties are bound via linkers to one targeting moiety, also referred to as the DAR.

A third aspect of the disclosure relates to a pharmaceutical composition comprising the stable cell targeting conjugates as described above and a pharmaceutically acceptable carrier.

In accordance with this disclosure, the term "pharmaceutical composition" relates to compositions comprising the stable cell targeting conjugates as described hereinabove. Such pharmaceutical compositions comprise a therapeutically effective amount of these stable cell targeting conjugates and a pharmaceutical acceptable carrier.

These pharmaceutical compositions may be administered with a physiologically acceptable carrier to a patient. The term "carrier" as used herein refers to a diluent, adjuvant, excipient, or vehicle with which the therapeutic is administered. Such pharmaceutical carriers can be sterile liquids, such as water. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

These pharmaceutical compositions can take the form of solutions, suspensions, emulsion, tablets. The composition can be formulated as a suppository, with traditional binders and carriers such as triglycerides.

Examples of suitable pharmaceutical carriers are described in "Remington's Pharmaceutical Sciences" by E. W. Martin. Such compositions will contain a therapeutically effective amount of the cell targeting conjugates, together with a suitable amount of carrier so as to provide the form for proper administration to the patient. The formulation should suit the mode of administration.

In another preferred embodiment, the pharmaceutical composition is formulated in accordance with routine procedures as a pharmaceutical composition adapted for intravenous administration to human beings. Typically, compositions for intravenous administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical grade organic or inorganic carriers and/or diluents suitable for oral and topical use can be used to make up compositions containing the therapeutically active compounds.

The compositions may also include one or more of the following:
carrier proteins such as serum albumin;
buffers;
fillers such as microcrystalline cellulose, lactose, corn and other starches;
binding agents;
sweeteners and other flavoring agents;
coloring agents; and
polyethylene glycol.

Additives are well known in the art, and are used in a variety of formulations.

A fourth aspect of the disclosure relates to the abovementioned stable cell targeting conjugates or the abovementioned pharmaceutical compositions, for use as a medicament. Preferably, the conjugates or pharmaceutical compositions thereof are used in the treatment of cancer, inflammation, fibrosis, metabolic disorders, central nervous system diseases, liver cirrhosis, end stage renal disease, infectious diseases or cardiovascular disorders.

The disclosure will now be illustrated by way of the following, non-limiting examples.

Example A) Effect of a Stripping Step with Thiourea on the Stability of Lx-Based Cell Targeting Conjugates Synthesis of NBD-4Py-Lx-Cl 1-(7-Nitrobenzo[c][1,2,5]oxadiazol-4-yl)piperidine-4-carboxylic acid 4-Chloro-7-nitrobenzofurazan (NBD) (500 mg, 2.51 mmol) in MeOH (20 ml) was added dropwise to a suspension of piperidine-4-carboxylic acid (971 mg, 7.52 mmol) and potassium carbonate (1.04 g, 7.52 mmol) in MeOH (15 ml) at 0° C. Once the addition was complete the ice-bath was removed and the reaction was stirred for 2 hours at which time all s.m. had been consumed according to TLC. The reaction mixture was concentrated to about 15 ml and cooled to 0° C. HCl (1 M, 25 ml) was carefully added resulting in the formation of a red suspension. The mixture was stirred for 10 minutes, filtered and washed with ice cold water (10 ml). The solid was recrystallized from hot MeOH to give the product (672 mg, 92%) as red needles. $^1$H-NMR (400 MHz, DMSO-$d_6$): δ 12.4 (br s, 1H), 8.45 (d, J=9.2 Hz, 1H), 6.66 (d, J=9.2 Hz, 1H), 4.66 (d, J=13.7 Hz, 2H), 3.67 (ddd, J=14.0, 11.2, 3.0 Hz, 2H), 2.76 (tt, J=10.3, 4.3 Hz, 1H), 2.11-2.03 (m, 2H) 1.76 (dtd, J=14.4, 10.9, 3.9 Hz, 2H). $^{13}$C-NMR (62.5 MHz, DMSO-$d_6$): δ 175.3, 145.2, 144.9, 144.7, 136.3, 120.6, 103.4, 49.2, 39.3, 27.9. HRMS (ESI$^+$) $C_{12}H_{12}N_4O_3Na$ [M+Na]$^+$ calc 315.0700. found 315.0687.

1-(7-Nitrobenzo[c][1,2,5]oxadiazol-4-yl)-N-(pyridin-4-ylmethyl)piperidine-4-carboxamide(NBD-4Py)

To a suspension of carboxylic acid NBD (194 mg, 0.664 mmol) and triethylamine (235 mg, 2.32 mmol) in MeCN (3 ml) at RT was added BOP (294 mg, 0.664 mmol). After 5 minutes, the suspension had largely cleared at which point 4-(methylamine)pyridine (71.8 mg, 0.664 mmol) in DCM (6 ml) was added. After stirring for 15 minutes, an orange precipitate formed which was stirred for 5 hours at RT. The reaction was diluted with DCM and washed with sat. aq. NaHCO$_3$. The water layer was extracted with DCM (3×) to dissolve all of the partially precipitated product, and the combined organic layers were washed with brine, dried with Na$_2$SO$_4$, filtered and evaporated onto silica gel. Purification by flash chromatography (1-5% MeOH in DCM) afforded the product (123 mg, 99%) as an orange-red solid. $^1$H-NMR (400 MHz, DMSO-$d_6$): δ 8.55 (t, J=6.0 Hz, 1H), 8.50-8.45 (m, 3H), 7.24-7.20 (m, 2H), 6.68 (d, J=9.3 Hz, 1H), 4.79 (d, J=13.4 Hz, 2H), 4.30 (d, J=6.0 Hz, 2H), 3.66-3.56 (m, 2H), 2.75 (tt, J=11.0, 4.4 Hz, 1H), 2.07-1.98 (m, 2H), 1.87-1.75 (m, 2H). $^{13}$C-NMR (62.5 MHz, DMSO-$d_6$): δ 173.7, 149.5, 148.6, 145.2, 144.9, 144.8, 136.4, 122.0, 120.6, 103.4, 49.4, 41.0, 40.7, 28.5. HRMS (ESI$^+$) $C_{18}H_{19}N_6O_4$ [M+H]$^+$ calc 383.1462. found 383.1490.

NBD-4Py-Lx-Cl

[Pt(en)Cl$_2$] (1 equiv.) was reacted with AgNO$_3$ (1 equiv.) in DMF (0.15 M) for 16 hours in the dark. The suspension was filtered over CELITE® and the filter rinsed with an equal amount of DMF. The NBD-4Py ligand (46.9 mg, 0.123 mmol) was then added as a solid to the filtrate and the mixture was stirred in the dark for 24 hours. The reaction was monitored by HPLC analysis and once no increase in conversion was observed, the reaction mixture was concentrated. The crude product was taken up in a mixture of 20 mM aq. NaCl and methanol and insoluble material was removed by filtration. Purification was performed by preparative reverse-phase HPLC. Product fractions were collected on ice and immediately frozen and lyophilized. $^1$H-NMR (400 MHz, methanol-$d_4$): δ 8.70-8.61 (m, 2H), 8.48 (d, J=9.0 Hz, 1H), 7.40 (d, J=6.8 Hz, 2H), 6.58 (d, J=9.3 Hz, 1H), 5.9 (br. s., 2H), 5.6 (br. s., 2H), 4.96-4.88 (m, 2H), 4.45 (s, 2H), 3.64-3.50 (m, J=2.7 Hz, 2H), 2.82 (tt, J=4.2, 11.2 Hz, 1H), 2.75-2.52 (m, 4H), 2.17-2.04 (m, 2H), 2.00-1.86 (m, 2H) $^{195}$Pt-NMR (86.0 MHz, methanol-$d_4$): δ −2507 ppm. HRMS (ESI$^+$) $C_{20}H_{26}ClN_8O_4Pt$ [M]$^+$ calc 672.1414. found 672.1384.

Conjugation of NBD-4Py-Lx-Cl to Trastuzumab

NBD-4Py-Lx-Cl (40 microliters, 5 mM in 20 mM NaCl, 20 equiv.) was added to a solution of trastuzumab, used in its commercial formulation, (71 microliters, 21 mg/ml) and tricine buffer (12.3 microliters, pH 8.47, 8 mM final concentration). The mixture was placed in a THERMO-MIXER® at 37° C. for 2 hours, followed by purification using a prewashed PD10 column which was eluted with PBS. With size exclusion chromatography (Phenomonex BioSep-SEC S 2000 column, elution phosphate buffer pH 6.8) conjugation was clearly observed. Furthermore, no aggregation was observed.

The number of NBD-4Py-Lx groups conjugated to trastuzumab was determined by overnight incubation of the purified conjugate at pH ~10.5, which resulted in complete hydrolysis of the NBD label to NBD-OH. Separation by SEC then allowed determination of the relative concentration of protein and NBD-OH at 280 and 472 nm, respectively. An NBD/mAb ratio of 3.1 was found.

Stability of NBD-4Py-Lx-Trastuzumab Conjugate

1) Untreated NBD-4Py-Lx-Trastuzumab Conjugate

Figure 1:
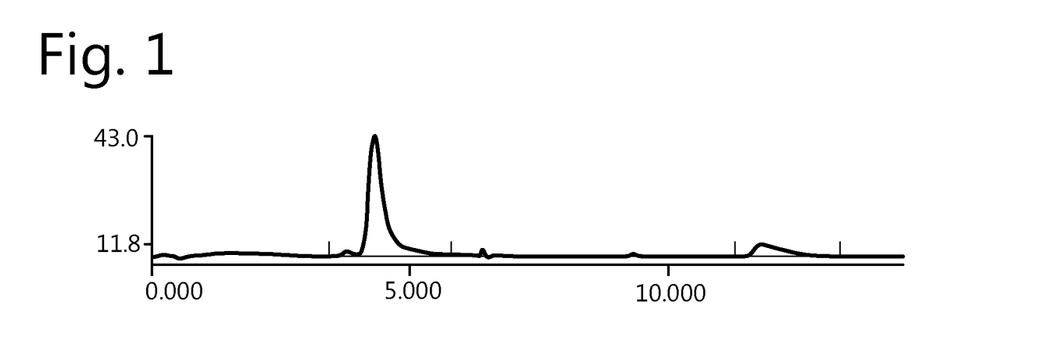
FIG. 1: Size exclusion chromatography (SEC) chromatogram of untreated NBD-4Py-Lx-trastuzumab conjugate.

The stability of the NBD-4Py-Lx-trastuzumab conjugate was determined by storing a composition comprising the conjugate (0.75 mg/ml) in PBS for 48 hours at room temperature. Analysis by SEC showed a partial release of the NBD-platinum linker complex. In FIG. 1, the SEC chromatogram is provided and from this it is clear that two peaks are present, the first and largest is the conjugate, but the second and smallest is detached NBD-platinum linker complex.

2) Trastuzumab-Complex 1 Conjugate Treated with Thiourea

Figure 2:
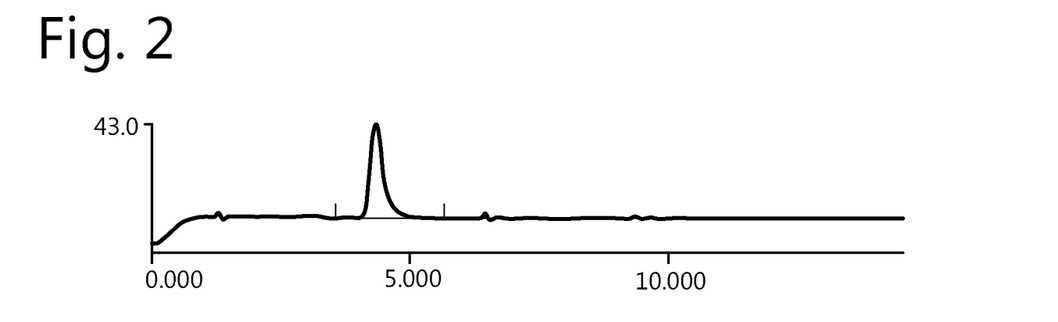
FIG. 2: SEC chromatogram of NBD-4Py-Lx-trastuzumab conjugate treated with thiourea.

NBD-4Py-Lx-trastuzumab conjugate was prepared under the same conditions as for experiment 1 above. However, prior to PD10 purification the crude reaction mixture was treated with thiourea for 30 minutes at 37° C. After purification by a PD10 column the conjugates were stored in PBS for 48 hours at room temperature. In FIG. 2, the SEC chromatogram is provided of this composition. From this chromatogram it is clear that there is only one peak and no detectable release of the NBD-platinum linker complexes from trastuzumab. In other words, the treatment with thiourea efficiently removed NBD-platinum complexes which were weakly bound to trastuzumab. It was further found that the NBD/mAB ratio was 2.0, which indeed shows that some of the NBD was removed by the thiourea treatment.

Example B) Effect of Thiourea on Lx Complexes Coordinated to Histidines or Methionines This example demonstrates the effect of stripping on the coordination bond of Lx with histidines or methionines using a histidine and a methionine-based model compound.

Fe-Desferal-4Py

N-succinyldesferal-Fe (prepared according Verel et al., *Journal of Nuclear Medicine* 2003, 1271-1281) (89 mg, 0.124 mmol) was dissolved in DMF (Volume: 1.2 ml) and HOBt (25.2 mg, 0.186 mmol), EDC (35.7 mg, 0.186 mmol), DIPEA (0.043 ml, 0.248 mmol) and pyridin-4-ylmethanamine (0.014 ml, 0.137 mmol) were sequentially added. The mixture was stirred for 20 hours, then concentrated after which the crude product was taken up in water and purified by SepPak C18-Plus columns. The product was eluted from the columns and lyophilized resulting in a dark red solid (yield 124 mg, 82.9%)

HRMS (ER$^+$) $C_{35}H_{56}FeN_8O_{10}$ [M+H]$^+$ calc 804.3463. found 804.3516.

Fe-Desferal-4Py-Lx-Cl

AgNO$_3$ (13.10 mg, 0.077 mmol) was added to a suspension of [Pt(en)Cl$_2$] (50 mg, 0.153 mmol) in DMF (1 ml). After stirring for 24 hours, the grey precipitate was filtered over CELITE®, which was then rinsed with DMF (1 ml). Of this solution, 1.1 eq of activated Pt was added to Fe-desferal-4Py (62 mg, 0.077 mmol). The mixture was stirred for 24 hours under argon after which HPLC indicated full conversion. The solvent was evaporated under reduced pressure after which the crude product was taken up in a mixture of water and methanol (4.5 ml). Purification was performed by preparative reverse-phase HPLC. Product fractions were collected on ice and immediately frozen and lyophilized resulting in a dark red solid (yield 36 mg, 42.6%).

HRMS (ESI$^+$) C$_{37}$H$_{63}$ClFeN$_{10}$O$_{10}$Pt [M+Na]$^{2+}$ calc 558.6652. found 558.6657.

HPLC (Alltima C18, 25×4.6 mm, 5 micrometer) indicated that the product was 99% pure (retention time 17.3, water/acetonitrile gradient 5 to 25% in 20 minutes measured at a wavelength of 430 nm).

Fe-Desferal-4Py-Lx-N-Acetyl-1-Histidine-Amide

N-Acetyl-L-histidine amide (45.8, 0.23 mmol) was added to a solution of Fe-desferal-4Py-LxCl (25 mg, 0.023 mmol) in 20 mM HEPES buffer pH 8.11 (3.0 ml). The mixture was stirred for 1.5 hours at 47° C. after which HPLC indicated ca. 80% conversion. The crude solution was purified by preparative reverse-phase HPLC. Product fractions were collected on ice and immediately frozen and lyophilized resulting in a dark red solid (yield 13 mg, 43.9%).

HPLC (Alltima C18, 25×4.6 mm, 5 micrometer) indicated that the product was 98% pure (retention time 16.3, water/acetonitrile gradient 5% to 25% in 20 minutes measured at a wavelength of 430 nm).

Fe-Desferal-4Py-Lx-N-Acetyl-L-Methionine-Amide

N-acetyl-1-methionine amide (43.7, 0.23 mmol) was added to as solution of Fe-desferal-4Py-Lx-Cl (25 mg, 0.023 mmol) in 20 mM HEPES buffer pH 8.11 (3.0 ml). The mixture was stirred for 1.5 hours at 47° C. after which HPLC indicated ca. 90% conversion. The crude solution was purified by preparative reverse-phase HPLC. Product fractions were collected on ice and immediately frozen and lyophilized resulting in a dark red solid (yield 9 mg, 30.6%).

HPLC (Alltima C18, 25×4.6 mm, 5 micrometer) indicated that the product was 98% pure (retention time 16.2, water/acetonitrile gradient 5% to 25% in 20 minutes measured at a wavelength of 430 nm).

The Lx-4Py-Desferal-Fe, Fe-desferal-4Py-N-Acetyl-L-histidine-amide and Fe-desferal-4Py-Lx-N-Acetyl-L-methionine-amide complexes (5 mM solution in 20 mM NaCl) were incubated with 1 volume equivalent thiourea solution (20 mM in water) for 2 hours at 37° C. after which the product was analyzed by reversed phase-HPLC. Whereas the retention times of Fe-desferal-4Py-Lx-Cl and Fe-desferal-4Py-Lx-N-Acetyl-L-methionine-amide shifted to 16.7 minutes after 2 hours incubation with thiourea, the retention time of the Fe-desferal-4Py-Lx-N-Acetyl-L-histidine-amide did not shift. This result indicates that both the Pt-chlorido and Pt-methionine coordination bond are replaced for thiourea whereas the Pt-histidine coordination bond is stable, i.e., weak methionine coordination bonds are stripped after a thiourea treatment.

Example C) Effect of the Stripping Agent Concentration and the Stripping Time on the Stripping of Weakly Bound Functional Moieties from Cell Targeting Conjugates NBD-4Py-Lx-Cl (40 microliters, 5 mM in 20 mM NaCl, 20 equiv.) was added to a solution of trastuzumab, used in its commercial formulation, (71 microliters, 21 mg/ml) and HEPES buffer (12.3 microliters, pH 7.47, 20 mM final concentration). The mixture was placed in a THERMO-MIXER® at 37° C. for 4 hours, followed by purification using a prewashed PD10 column which was eluted with 0.9% NaCl. With size exclusion chromatography conjugation was clearly observed. Furthermore no aggregation was observed. An NBD/mAb ratio of 4.1 was found.

To determine the effect of the stripping agent concentration and the stripping time, the purified conjugate was incubated with 1 volume equivalent thiourea solution with concentrations ranging from 5 to 50 mM (final concentration)) in a THERMOMIXER® at 37° C. with incubation times ranging from 5 to 60 minutes. As a control, the conjugate was also incubated with PBS.

The percentage of released NBD label (excitation and emission wavelength of 485 nm and 535 nm, respectively) was determined spectrophotometrically. The conjugation mixture was precipitated with 2 volume equivalents acetonitrile followed by centrifugation of the formed suspension (5 minutes, 14K rpm). By measuring the fluorescence of the supernatant, the percentage of released NBD label was determined.

Figure 3:
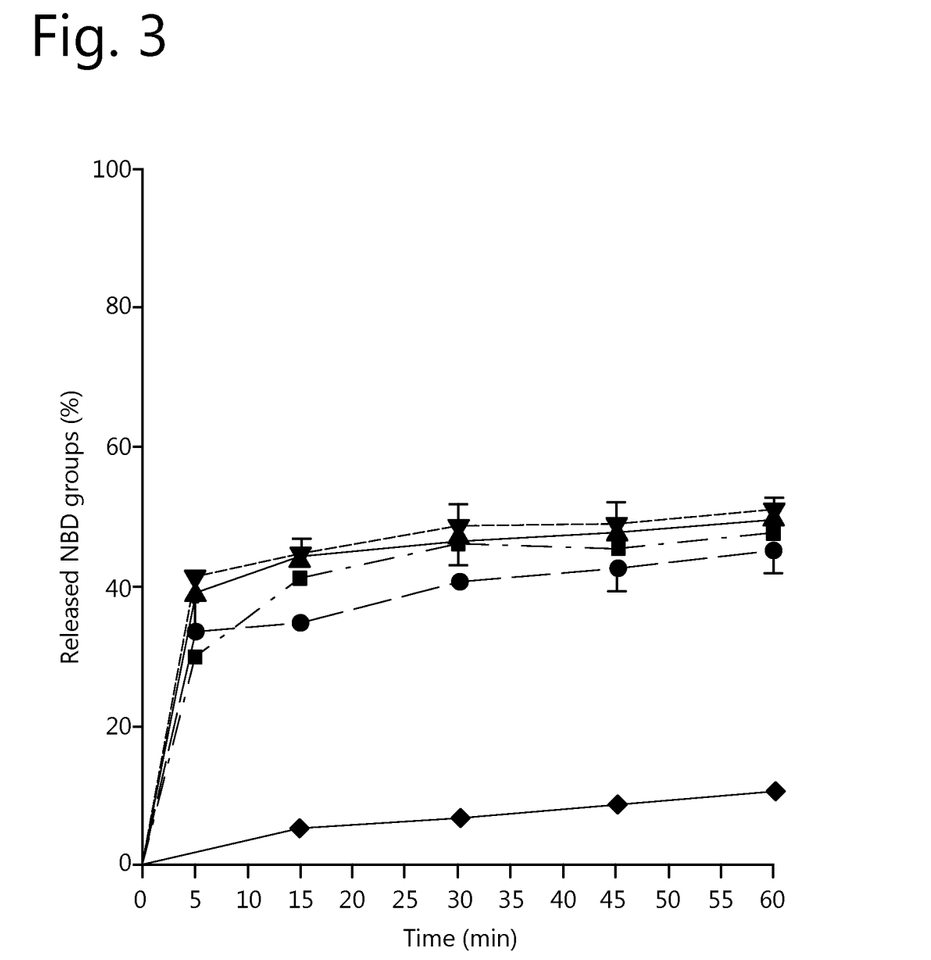
FIG. 3: Effect of stripping agent concentration and stripping time on the removal of weakly bound functional moieties from cell targeting conjugates. Legend: ● 5 mM thiourea; ■ 10 mM thiourea; ▲ 25 mM thiourea; ▼ 50 mM thiourea; ♦ PBS.

In FIG. 3, the percentage of released NBD groups as a function of time is provided for several stripping agent concentrations. From this graph it is clearly visible that a plateau is reached after 30 minutes for a stripping agent concentration of above 10 mM. In other words, after 30 minutes stripping time all weakly bound NBD has been removed from the conjugate. Furthermore, it can be clearly observed that the addition of thiourea in the stripping step speeds up the removal of weakly bound NBD-Lx from trastuzumab and ensures that the removal is quantitative.

Example D) Effect of a Variety of Sulfur or Nitrogen Donors on the Stripping Efficiency of Weakly Bound Functional Moieties from Cell Targeting Conjugates This example demonstrate for a variety of sulfur (S)-donors and a nitrogen (N)-donor, the efficiency of removing weakly bound moieties from an antibody during the post treatment step. The following S-donors were selected, n-acetyl-1-methionine, 1-cysteine, sodium thiosulfate (STS), and potassium thiocyanate (KSCN). Histidine was chosen as a N-donor. These agents appeared to be incapable of breaking the coordination bond between the NBD-4Py and the Lx.

NBD-4Py-Lx-Cl (133 microliters, 5 mM in 20 mM NaCl, 20 equiv.) was added to a solution of trastuzumab, used in its commercial formulation, (238 microliters, 21 mg/ml) and HEPES buffer (12.3 microliters, pH 7.47, 20 mM final concentration). The mixture was placed in a THERMO-MIXER® at 37° C. for 4 hours, followed by purification using a prewashed PD10 column which was eluted with 0.9% NaCl. The purified conjugate was incubated with PBS or the S and N-donors as listed above (10 mM final concentration) in a THERMOMIXER® at 37° C. for 30 minutes. With size exclusion chromatography conjugation was clearly observed. Furthermore no aggregation was observed. The NBD/mAb ratio of all the conjugates were between 4.0 and 4.2.

The percentage of the released NBD label was determined as described in Example B.

TABLE 1

Release of NBD-Lx after 30 minutes stripping for a variety of S- and N-donors.

| Agent | Released label (%) |
|---|---|
| PBS | 6.7 |
| Thiourea | 46.3 |
| N-acetyl-1-methionine | 12.2 |
| L-cysteine | 36.4 |
| NaSTS | 52.4 |
| KSCN | 35.9 |
| Histidine | 5.9 |

As revealed in Table 1, all S-donors show an improvement in the percentage of released label during the stripping step compared to PBS and histidine. This example indicates that for an efficient removal of weakly bound Lx complexes from an antibody an S-donor is needed. Thiourea and STS appear to be the best stripping agents.

Example E) Effect of the Stripping Step on Cell Targeting Conjugates Comprising NBD Prepared with Varying Conjugation Times This example demonstrates the effect of the stripping step on the removal of weakly bound moieties from trastuzumab for conjugates prepared with varying conjugation times.

NBD-4Py-Lx-Cl (133 microliters, 5 mM in 20 mM NaCl, 20 equiv.) was added to a solution of trastuzumab, used in its commercial formulation, (238 microliters, 21 mg/ml) and HEPES buffer (12.3 microliters, pH 7.47, 20 mM final concentration). The mixture was placed in a THERMO-MIXER® at 37° C. for 2, 4, 6 and 24 hours, followed by purification using a prewashed PD10 column which was eluted with 0.9% NaCl. The purified conjugate was incubated with thiourea (10 mM final concentration) in a THERMOMIXER® at 37° C. for 30 minutes.

The percentage of the released NBD label was determined as described in Example B (see Table 2). With size exclusion chromatography conjugation was clearly observed. Furthermore no aggregation was observed.

TABLE 2

The effect of the stripping step on the removal of weakly bound NBD-Lx from trastuzumab prepared with varying conjugation times.

| Conjugation time (h) | Released label (%) |
|---|---|
| 2 | 47.1 |
| 4 | 48.0 |
| 6 | 44.8 |
| 24 | 32.0 |

The decreased percentage of released NBD-4Py-Lx indicates that the stability of the conjugate increases with increasing conjugation time. However, a stripping step is still important to obtain a stable cell targeting conjugate.

Example F) Effect of the Stripping Step on Cell Targeting Conjugates Comprising Desferal Prepared with Varying Conjugation Times

Fe-Desferal-Pip

N-Succinyldesferal-Fe (prepared according Verel et al., *Journal of Nuclear Medicine* 2003, 1271-1281) (150 mg, 0.210 mmol) was dissolved in DMF (Volume: 2.5 ml) and HOBt (42.6 mg, 0.315 mmol), EDC (60.4 mg, 0.315 mmol), DIPEA (36 microliters, 0.315 mmol) and tert-butyl 4-(aminomethyl)piperidine-1-carboxylate (45 mg, 0.210 mmol) were sequentially added. The reaction was stirred for 20 hours and subsequently concentrated. A C18-EC column (10 g) and a SepPak C18-Plus cartridge were activated with methanol (20 ml and 6 ml, respectively) and washed with water (200 ml and 60 ml, respectively). The crude product was taken up in water (10 ml) but did not fully dissolve. The solution was loaded on the C18-EC column and the residue was dissolved in methanol (1 ml) and diluted with water (50 ml), this solution was loaded on the SepPak C18-Plus cartridge that was then connected to the outlet of the C18-EC column. The setup was washed with water (250 ml) and the product was eluted with ca. 15 ml of MeCN. The product fraction was diluted with an equal volume of water and lyophilized to give a dark red solid.

HRMS (ESI+) $C_{40}OH_{69}FeN_8O_{12}$ [M+H]+ calc 910.4457. found 910.4464.

The freeze-dried product was dissolved in 4 ml DCM/TFA (1:1) and stirred for 75 minutes at RT. Subsequently, the reaction mixture was concentrated after which the solid was dissolved in 10 ml of water and freeze-dried. The freeze-dried product was dissolved in methanol and charged on one SCX-2 2G column that had been activated with methanol before. The column was washed three times with 0.25 M ammonia in methanol and eluted with three times 1 N ammonia in methanol and 40 ml 7 N ammonia in methanol after which the solution was concentrated affording a brown solid (142 mg, 84%).

HRMS (ESI+) $C_{35}H_{61}FeN_8O_{10}$ [M+H]+ calc 810.3933. found 810.4002.

Fe-desferal-Pip-LxCl

AgNO$_3$ (27.0 mg, 0.153 mmol) was added to a suspension of [Pt(en)Cl$_2$] (50 mg, 0.153 mmol) in DMF (1 ml) and stirred for 16 hours at RT. The mixture was filtered over CELITE® and the filter was rinsed with 1 ml of DMF. Subsequently, 0.78 ml of the solution (0.062 mmol) was added to Fe-desferal-Pip (50 mg, 0.062 mmol) and the mixture was stirred for 16 hours at RT under the protection of light followed by removal of the solvent under reduced pressure. The solvent was evaporated under reduced pressure after which the crude was taken up in a mixture of water and methanol (4.5 ml). Purification was performed by preparative reverse-phase HPLC. Product fractions were collected on ice and immediately frozen and lyophilized resulting in a dark red solid (yield 25 mg, 37.0%).

HRMS (ESI+) C$_{37}$H$_{69}$ClFeN$_{10}$O$_{10}$Pt [M+H]$^+$ calc 1100.3910. found 1100.3694.

Fe-Desferal-Pip-Lx-Trastuzumab

Lx-Pip-desferal-Fe (5 microliters, 5 mM in 20 mM NaCl, 5 equiv.) was added to a solution of trastuzumab, used in its commercial formulation, (35.5 microliters, 21 mg/ml) and HEPES buffer (4.5 microliters, pH 8.11, 10 mM final concentration). The mixture was placed in a THERMOMIXER® at 37° C. for 1, 2, 4 and 6 hours after which the reaction mixture was incubated with thiourea (45 microliters, 10 mM final concentration) in a THERMOMIXER® at 37° C. for 30 minutes (sample A). The samples were analyzed by SEC (Phenomonex BioSep-SEC S 2000 column, elution phosphate buffer pH 6.8). In another experiment, the conjugation was directly analyzed with SEC (sample B). The percentage of conjugated desferal was calculated by dividing the area of the antibody peak with the total peak area (iron channel at 430 nm). The results of this analysis are shown in Table 3.

TABLE 3

The effect of the stripping step on the removal of weakly bound Fe-desferal-Pip-Lx from trastuzumab

| | Sample A | | Sample B |
|---|---|---|---|
| time (h) | Percentage of Fe-desferal-Pip-Lx bound to trastuzumab (%) | time (h) | Percentage of Fe-desferal-Pip-Lx bound to trastuzumab (%) |
| 1 | 4.5 | 1 | 9.4 |
| 2 | 7.7 | 2 | 15.8 |
| 4 | 13.9 | 4 | 22.2 |
| 6 | 20.3 | 6 | 28.7 |
| 24 | 43.0 | 24 | 44.0 |

The decreased percentage of Fe-desferal-Pip-Lx bound to trastuzumab after stripping indicates that a significant percentage of Fe-desferal-Pip-Lx conjugated to the antibody is weakly bound after the conjugation.

Example G) Stability of a $^{89}$Zr-Desferal-4Py-Lx-Trastuzumab Conjugate

This example demonstrates the effect of a stripping step on the stability of a cell targeting moiety during incubation with bovine serum albumin (BSA).

$^{89}$Zr-Desferal-4Py-Lx-Trastuzumab

Fe-Desferal-4Py-Lx-Cl (40 microliters, 5 mM in 20 mM NaCl, 20 equiv.) was added to a solution of trastuzumab, used in its commercial formulation, (71 microliters, 21 mg/ml) and tricine buffer (12.3 microliters, pH 8.47, 8 mM final concentration). The mixture was placed in a THERMOMIXER® at 37° C. for 24 hours after which the reaction mixture was incubated with thiourea (123 microliters, 10 mM final concentration) in a THERMOMIXER® at 37° C. for 30 minutes followed by purification using a pre-washed PD10 column, which was eluted with 0.9% NaCl (sample A). In another experiment, the conjugation was directly purified by PD10 (sample B). The obtained 4Py-desferal-Fe-Lx-trastuzumab conjugates were radio-labelled with $^{89}$Zr using published procedures (Verel et al., *Journal of Nuclear Medicine* 2003, 1271-1281) to afford $^{89}$Zr-desferal-4Py-Lx-trastuzumab. With size exclusion chromatography, conjugation was clearly observed. Furthermore, no aggregation was observed.

$^{89}$Zr-Desferal-4Py-Lx-trastuzumab was incubated with BSA (45 g/ml final concentration) at 37° C. and at several time points a sample was taken and analyzed with SEC (radioactivity channel). The stability of the conjugate was determined by comparing the area of peak of $^{89}$Zr-Desferal-Lx bound to trastuzumab to the total peak area ($^{89}$Zr-desferal-Lx bound to trastuzumab+$^{89}$Zr-desferal-Lx bound to BSA+free $^{89}$Zr-desferal-Lx). The results of this analysis are shown in Table 4.

TABLE 4

Stability of $^{89}$Zr-desferal-Lx-trastuzumab in BSA

| Sample A | | Sample B | |
|---|---|---|---|
| time (h) | Percentage $^{89}$Zr-desferal-Lx bound to trastuzumab (%) | time (h) | Percentage $^{89}$Zr-desferal-Lx bound to trastuzumab (%) |
| 0 | 100.0 | 0 | 100.0 |
| 22 | 97.5 | 22 | 93.2 |
| 71 | 97.5 | 114 | 86.4 |
| 189 | 96.4 | 162 | 85.9 |
| 239 | 97.9 | 284 | 86.1 |
| 359 | 95.0 | 354 | 83.8 |

As shown in Table 4, the conjugate that was prepared including a thiourea stripping step (sample A) is more stable in BSA with respect to release of $^{89}$Zr-Desferal label over time compared to its analogue that was not treated with thiourea (Sample B).

The invention claimed is:

1. Stable cell targeting conjugates produced by a method comprising:
    treating a composition of cell targeting conjugates with thiourea such that weakly bound functional moieties are removed from the cell targeting conjugates so as to obtain a composition comprising stable cell targeting conjugates,
    wherein the cell targeting conjugates comprise a targeting moiety and at least one functional moiety bound thereto via a linker comprising a transition metal complex, and
    wherein the stable cell targeting conjugates have had weakly bound functional moieties removed therefrom as may be determined by storing a composition of the stable cell targeting conjugates in phosphate-buffered saline at room temperature for 48 hours, and afterwards, applying size exclusion chromatography to the composition, and wherein no significant amount of detached functional moiety or functional moiety-linker complex is observed in the composition in comparison to untreated conjugates.

2. Stable cell targeting conjugates produced by a method comprising:
    treating a composition of cell targeting conjugates with an agent that removes weakly bound functional moieties from the cell targeting conjugates so as to obtain a composition comprising stable cell targeting conjugates,
    wherein the cell targeting conjugates comprise a targeting moiety and at least one functional moiety bound thereto via a linker comprising a transition metal complex, and
    wherein the stable cell targeting conjugates have a serum stability that is at least two times greater than the serum stability of untreated conjugates.

3. The stable cell targeting conjugates of claim 2, wherein the linker comprises a platinum complex.

4. The stable cell targeting conjugates of claim 2, wherein the linker comprises a cis-platinum complex.

5. The stable cell targeting conjugates of claim 2, wherein the relative binding affinity of the agent for the linker is less than the relative binding affinity of the linker for histidine.

6. The stable cell targeting conjugates of claim 2, wherein the agent is a competitor S-donor compound.

7. The stable cell targeting conjugates of claim 2, wherein the agent comprises thiourea, sodium thiosulphate (STS), glutathione, cysteine, N-acetylcysteine, potassium thiocyanate, sodium thiocyanate, biotin, methionine, n-acetyl-methionine penicillamine, mesna, or combinations of any thereof.

8. The stable cell targeting conjugates of claim 2, wherein the targeting moiety is a peptide, an antibody, an antibody fragment or engineered variant thereof.

9. The stable cell targeting conjugates of claim 2, wherein the at least one functional moiety is a therapeutic compound, a diagnostic compound or a chelating agent.

10. A pharmaceutical composition comprising:
    the stable cell targeting conjugates according to claim 1; and
    a pharmaceutically acceptable carrier.

11. The stable cell targeting conjugates of claim 3, wherein the platinum complex is a cis-platinum complex comprising an inert bidentate moiety.

12. The stable cell targeting conjugates of claim 1, wherein the method comprises:
    treating the composition of cell targeting conjugates with thiourea for 10 to 240 minutes.

13. A pharmaceutical composition comprising:
    the stable cell targeting conjugates of claim 2; and
    a pharmaceutically acceptable carrier.

* * * * *

UNITED STATES PATENT AND TRADEMARK OFFICE
CERTIFICATE OF CORRECTION

PATENT NO. : 10,668,168 B2
APPLICATION NO. : 15/556764
DATED : June 2, 2020
INVENTOR(S) : Van Dongen et al.

Page 1 of 1

It is certified that error appears in the above-identified patent and that said Letters Patent is hereby corrected as shown below:

On the Title Page
In ITEM (72)   Line 5   change "Umuiden (NL);" to --IJmuiden (NL);--

Signed and Sealed this
First Day of September, 2020

Andrei Iancu
*Director of the United States Patent and Trademark Office*